United States Patent
Hauck et al.

(10) Patent No.: US 7,263,397 B2
(45) Date of Patent: Aug. 28, 2007

(54) METHOD AND APPARATUS FOR CATHETER NAVIGATION AND LOCATION AND MAPPING IN THE HEART

(75) Inventors: John A. Hauck, Shoreview, MN (US); Jeff A. Schweitzer, St. Paul, MN (US); Michael Craven, St. Paul, MN (US); Valtino Afonso, Oakdale, MN (US); Holly Cotner, St. Paul, MN (US); Frank Callaghan, Blaine, MN (US); John Schultz, Elk River, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 524 days.

(21) Appl. No.: 10/819,027

(22) Filed: Apr. 6, 2004

(65) Prior Publication Data
US 2004/0254437 A1    Dec. 16, 2004

Related U.S. Application Data

(63) Continuation-in-part of application No. 09/107,371, filed on Jun. 30, 1998.

(60) Provisional application No. 60/461,004, filed on Apr. 7, 2003.

(51) Int. Cl.
*A61B 5/042* (2006.01)
(52) U.S. Cl. ....................... 600/374; 600/509
(58) Field of Classification Search ............... 600/374, 600/509
See application file for complete search history.

(56) References Cited

U.S. PATENT DOCUMENTS

| | | |
|---|---|---|
| 3,954,098 A | 5/1976 | Dick et al. |
| 4,173,228 A | 11/1979 | Van Steenwyk et al. |
| 4,304,239 A | 12/1981 | Perlin |
| 4,380,237 A | 4/1983 | Newbower |
| 4,431,005 A | 2/1984 | McCormick |
| 4,444,195 A | 4/1984 | Gold |
| 4,478,223 A | 10/1984 | Allor |
| 4,522,212 A | 6/1985 | Gelinas et al. |
| 4,559,951 A | 12/1985 | Dahl et al. |
| 4,572,186 A | 2/1986 | Gould et al. |
| 4,572,206 A | 2/1986 | Geddes et al. |
| 4,573,473 A | 3/1986 | Hess |
| 4,613,866 A | 9/1986 | Blood |
| 4,628,937 A | 12/1986 | Hess et al. |
| 4,641,649 A | 2/1987 | Walinsky et al. |
| 4,649,924 A | 3/1987 | Taccardi |

(Continued)

OTHER PUBLICATIONS

Arisi, G., et al., "Localization Of Ectopic Ventricular Focuses By Means Of A Diameter Multielectrode Catheter," *Advances in Electrocardiology*, Elsevier Science Publishers B.V. (Biomedical Division), Z. Antaloczy et al., editors, pp. 67-70 (1990).

(Continued)

*Primary Examiner*—Lee S. Cohen

(57) ABSTRACT

A medical system for finding and displaying the location of electrodes within the body. The electrodes may be used to measure the voltage on the heart wall and display this as an activation map on a geometry representing the heart chamber.

4 Claims, 9 Drawing Sheets

U.S. PATENT DOCUMENTS

| | | | |
|---|---|---|---|
| 4,660,571 A | 4/1987 | Hess et al. |
| 4,674,518 A | 6/1987 | Salo |
| 4,697,595 A | 10/1987 | Breyer et al. |
| 4,699,147 A | 10/1987 | Chilson et al. |
| 4,706,670 A | 11/1987 | Andersen et al. |
| 4,721,115 A | 1/1988 | Owens |
| 4,777,955 A | 10/1988 | Brayton et al. |
| 4,821,731 A | 4/1989 | Martinelli et al. |
| 4,840,182 A | 6/1989 | Carlson |
| 4,890,623 A | 1/1990 | Cook et al. |
| 4,898,176 A | 2/1990 | Petre |
| 4,898,181 A | 2/1990 | Kessler |
| 4,899,750 A | 2/1990 | Ekwall |
| 4,911,174 A | 3/1990 | Pederson et al. |
| 4,922,912 A | 5/1990 | Watanabe |
| 4,940,064 A | 7/1990 | Desai |
| 4,945,305 A | 7/1990 | Blood |
| 4,945,342 A | 7/1990 | Steinemann |
| 4,951,682 A | 8/1990 | Petre |
| 5,000,190 A | 3/1991 | Petre |
| 5,005,587 A | 4/1991 | Scott |
| 5,025,786 A | 6/1991 | Siegel |
| 5,029,588 A | 7/1991 | Yock et al. |
| 5,042,486 A | 8/1991 | Pfeiler et al. |
| 5,054,492 A | 10/1991 | Scribner et al. |
| 5,054,496 A | 10/1991 | Wen et al. |
| 5,056,517 A | 10/1991 | Fenici |
| 5,058,583 A | 10/1991 | Geddes et al. |
| 5,081,993 A | 1/1992 | Kitney et al. |
| 5,090,411 A | 2/1992 | Higuchi |
| 5,156,151 A | 10/1992 | Imran |
| 5,158,092 A | 10/1992 | Glace |
| 5,161,536 A | 11/1992 | Vilkomerson et al. |
| 5,211,165 A | 5/1993 | Dumoulin et al. |
| 5,220,924 A | 6/1993 | Frazin |
| 5,228,442 A | 7/1993 | Imran |
| 5,237,996 A | 8/1993 | Waldman et al. |
| 5,255,678 A | 10/1993 | Deslauriers et al. |
| 5,273,038 A | 12/1993 | Beavin |
| 5,282,471 A | 2/1994 | Sato |
| 5,295,484 A | 3/1994 | Marcus et al. |
| 5,297,549 A | 3/1994 | Beatty et al. |
| 5,305,745 A | 4/1994 | Zacouto |
| 5,311,866 A | 5/1994 | Kagan et al. |
| 5,323,781 A | 6/1994 | Ideker et al. |
| 5,324,284 A | 6/1994 | Imran |
| 5,325,860 A | 7/1994 | Seward et al. |
| 5,341,807 A | 8/1994 | Nardella |
| 5,345,936 A | 9/1994 | Pomeranz et al. |
| 5,360,006 A | 11/1994 | Geiser et al. |
| 5,372,138 A | 12/1994 | Crowley et al. |
| 5,377,678 A | 1/1995 | Dumoulin et al. |
| 5,385,146 A | 1/1995 | Goldreyer |
| 5,391,199 A | 2/1995 | Ben-Haim |
| 5,409,000 A | 4/1995 | Imran |
| 5,411,025 A | 5/1995 | Webster, Jr. |
| 5,433,198 A | 7/1995 | Desai |
| 5,458,126 A | 10/1995 | Cline et al. |
| 5,551,426 A | 9/1996 | Hummel et al. |
| 5,553,611 A | 9/1996 | Budd et al. |
| 5,558,091 A | 9/1996 | Acker et al. |
| 5,588,432 A | 12/1996 | Crowley |
| 5,601,084 A | 2/1997 | Sheehan et al. |
| 5,622,174 A | 4/1997 | Yamazaki |
| 5,662,108 A | 9/1997 | Budd et al. |
| 5,669,382 A | 9/1997 | Curwen et al. |
| 5,687,737 A | 11/1997 | Branham et al. |
| 5,697,377 A | 12/1997 | Wittkampf |
| 5,701,897 A | 12/1997 | Sano |
| 5,713,363 A | 2/1998 | Seward et al. |
| 5,722,402 A | 3/1998 | Swanson et al. |
| 5,738,096 A | 4/1998 | Ben-haim |
| 5,797,396 A | 8/1998 | Geiser et al. |
| 5,824,005 A | 10/1998 | Motamedi et al. |
| 5,840,031 A | 11/1998 | Crowley |
| 5,846,198 A | 12/1998 | Killmann |
| 5,848,972 A | 12/1998 | Triedman et al. |
| 5,871,019 A | 2/1999 | Belohlavek |
| 5,908,446 A | 6/1999 | Imran |
| 6,004,269 A | 12/1999 | Crowley et al. |
| 6,095,976 A | 8/2000 | Nachtomy et al. |
| 6,603,996 B1 | 8/2003 | Beatty et al. |
| 6,990,370 B1 * | 1/2006 | Beatty et al. ............... 600/509 |

OTHER PUBLICATIONS

Branham B., et al., "A System For Accurate Interactive 3-D Display Of Cardiac Electrical Activity," *Computers in Cardiology,* IEEE Computer Society Press 0276-6547/92, pp. 335-338 (Oct. 11-14, 1992).

Breyer, B. and Cikes, I., "Ultrasonically Marked Catheter—A Method For Positive Echographic Catheter Position Identification," *Med. & Biol. Eng. & Comput.,* 22:268-271 (May 1984).

Buckles, D., et al., "Computer-Enhanced Mapping Of Activation Sequences In The Surgical Treatment Of Supraventricular Arrhythmias, " *PACE,* vol. 13, Part I, pp. 1401-1407 (Nov. 1990).

Cikes, I., et al., "Cardiac Catheterisation Guided By Ultrasound," *Journal of the American College of Cardiology,* vol. 3, No. 2, p. 564 (Feb. 1984).

Cikes, I. and Breyer, B., "Complete Cardiac Catheterisation Guided By Ultrasound," *European Heart Journal,* vol. 4 (suppl. E), p. 21 (1983).

Cikes I., "Interventional Echocardiography," *5th Symposium on Echocardiology,* Rotterdam, Abstracts p. 38 (1983).

Cikes, I., et al., "Interventional Echocardiography," *Interventional Ultrasound,* 1st edition, chapter 25, Munksgaard, Copenhagen, pp. 160-168 (1985).

Cox, J., et al., "Surgery For Atrial Fibrillation," *Cardiac Surgery: State of the Art Reviews,* vol. 4, No. 1, pp. 207-217 (1990).

De Bakker, J., et al., "Endocardial Mapping By Simultaneous Recording Of Endocardial Electrograms During Cardiac Surgery For Ventricular Aneurysm," *Journal of American College of Cardiology,* vol. 2, No. 5, pp. 947-953 (Nov. 1983).

Derfus, D. and Pilkington, T., "Assessing The Effect Of Uncertainty In Intracavitary Electrode Position On Endocardial Potential Estimates," *IEEE Transactions on Biomedical Engineering,* vol. 39, No. 7, pp. 676-681 (Jul. 1992).

Derfus, D., et al., "Calculating Intracavitary Potentials from Measured Endocardial Potentials," *Annual International Conference of the IEEE Engineering in Medicine and Biology Society,* vol. 12, No. 2, p. 635 (1990).

Derfus, D., et al. "A Comparison of Measured and Calculated Intracavitary Potentials for Electrical Stimuli in the Exposed Dog Heart," *IEEE Transactions on Biomedical Engineering,* vol. 39, No. 11, pp. 1192-1206 (Nov. 1992).

Derfus, D. and Pilkington, T., "Effect Of Intracavitary Electrode Position On Endocardial Potential Estimates," *IEEE Engineering in Medicine & Biology Society 10th Annual International Conference,* pp. 185-186 (1988).

Desai, J., et al., "Orthogonal Electrode Catheter Array for Mapping of Endocardial Focal Site of Ventricular Activation," *PACE,* vol. 14, Part I, pp. 557-574 (Apr. 1991).

Downar, E., et al., "Endocardial Mapping of Ventricular Tachycardia in the Intact Human Ventricle: Evidence for Reentrant Mechanisms," *Journal of the American College of Cardiology,* vol. 11, No. 4, pp. 783-791 (Apr. 1988).

Durrer, D. and Van Der Tweel, L., "Spread of Activation in the Left Ventricular Wall of the Dog. II.: Activation Conditions at the Epicardial Surface," *American Heart Journal,* pp. 192-203 (Aug. 1953).

Fann, J., et al., "Endocardial Activation Mapping and Endocardial Pace-Mapping Using a Balloon Apparatus," *Am. J. Cardiol.,* vol. 55, pp. 1076-1083 (1985).

Fenici, R. and Melillo, G., "Biomagnetically Localizable Multipurpose Catheter And Method For MCG Guided Intracardiac Electrophysiology, Biopsy And Ablation Of Cardiac Arrhythmias," *International Journal of Cardiac Imaging*, vol. 7, pp. 207-215 (1991).

Fenici, R., et al., "Catheter Ablation Of Cardiac Arrhythmias: Magnetocardiographic Localization Of Electrocatheters And Arrhythmogenic Foci," *8th International Congress "The New Frontiers of Arrhythmias,"* Marilleva, Italy, pp. 723-731 (Jan. 31-Feb. 6, 1988).

Fenici, R., et al., "Clinical Magnetocardiography: 10 Years Experience At The Catholic University," *International Journal of Cardiac Imaging*, vol. 7, pp. 151-167 (1991).

Fenici, R. and Melillo, G., "Magnetocardiography: Ventricular Arrhythmias," *European Heart Journal*, vol. 14 (Suppl. E), pp. 53-60 (1993).

Harada, A., et al., "Potential Distribution Mapping: New Method For Precise Localization Of Intramural Septal Origin Of Ventricular Tachycardia," *Circulation*, vol. 78 (Suppl. III), No. 5, pp. III-137-III-147 (Nov. 1988).

Hauer, R., et al., "Endocardial Catheter Mapping: Validation Of A Cineradiographic Method For Accurate Localization Of Left Ventricular Sites," *Circulation*, vol. 74, No. 4, pp. 862-868 (Oct. 1986).

Hauer, R., et al. "Endocardial Catheter Mapping: Wire Skeleton Technique For Representation Of Computed Arrhythmogenic Sites Compared With Intraoperative Mapping," *Circulation*, vol. 74, No. 6, pp. 1346-1354 (Dec. 1986).

Ideker, R., et al., "A Computerized Method For The Rapid Display Of Ventricular Activation During The Intraoperative Study Of Arrhythmias," *Circulation*, vol. 59, No. 3, pp. 449-458 (Mar. 1979).

Ideker, R., et al., "Simultaneous Multichannel Cardiac Mapping Systems," *PACE*, vol. 10, pp. 281-292 (Mar.-Apr. 1987).

Ideker, R., "A Study To Evaluate The Ability Of A Multielectrode Intracavitary Probe To Determine The Site Of Origin Of Ventricular Tachycardia," *Basic Arrhythmia Laboratory, Engineering Research Center in Emerging Cardiovascular Technologies*, Duke University, pp. 1-3.

Jackman, W., et al., "New Catheter Technique For Recording Left Free-Wall Accessory Atrioventricular Pathway Activation: Identification Of Pathway Fiber Orientation," *Circulation*, vol. 78, No. 3, pp. 598-611 (Sep. 1988).

Josephson, M., *Clinical Cardiac Electrophysiology: Techniques and Interpretations*, 2nd ed., pp. 566-580, 608-615, and 770-783 (1993).

Josephson, M., et al., "Comparison Of Endocardial Catheter Mapping With Intraoperative Mapping Of Ventricular Tachycardia," *Circulation*, vol. 61, No. 2, pp. 395-404 (Feb. 1980).

Josephson, M., et al., "Role Of Catheter Mapping In Evaluation Of Ventricular Tachycardia," *Ventricular Tachycardia—Mechanisms And Management*, pp. 309-330, Mt. Kisco, NY: Futura Publishing Co. (1982).

Josephson, M., et al., "Role Of Catheter Mapping In The Preoperative Evaluation Of Ventricular Tachycardia," *American Journal of Cardiology*, vol. 40, pp. 207-220 (Jan. 1982).

Josephson, M., et al., "Ventricular Activation During Ventricular Endocardial Pacing. II. Role Of Pace-Mapping To Localize Origin Of Ventricular Tachycardia," *The American Journal of Cardiology*, vol. 50, pp. 11-22, (Jul. 1982).

Kaltenbrunner, W., et al., "Epicardial And Endocardial Mapping Of Ventricular Tachycardia In Patients With Myocardial Infarction: Is The Origin Of The Tachycardia Always Subendocardially Localized?," *Circulation*, vol. 84, No. 3, pp. 1058-1071 (Sep. 1991).

Khoury, D. and Rudy, Y., "A Model Study Of Volume Conductor Effects On Endocardial And Intracavitary Potentials," *Circulation Research*, vol. 71, No. 3, pp. 511-525 (Sep. 1992).

Khoury D. and Rudy, Y., "Reconstruction Of Endocardial Potentials From Intracavitary Probe Potentials: A Model Study," IEEE 0276-6547/92, pp. 9-12 (1992).

Kun, S. and Peura, R., "Conductance Volumetric Model Of An Eccentrically Positioned Catheter Within A Three-Compartment Ellipsoidal Ventricle," *IEEE Transactions on Biomedical Engineering*, vol. 40, No. 6, pp. 589-592 (Jun. 1993).

Langberg, J., et al., "The Echo-Transponder Electrode Catheter: A New Method For Mapping The Left Ventricle," *Journal of the American College of Cardiology*, vol. 12, pp. 218-223 (Jul. 1988).

Laxer, C., et al., "A Graphical Display System For Animating Mapped Cardiac Potentials," *Third Annual IEEE Symposium on Computer-Based Medical Systems*, IEEE Computer Society, pp. 197-204 (1990).

Lu, S. and Eiho, S., "Compound 3-D Visualization Of Reconstructed Coronary Arteries, Left Ventricle And Aorta From Biplane X-Ray Angiograms," *Computers in Cardiology*, IEEE Computer Society Press, 0276-6547/92, pp. 535-538 (Oct. 11-14, 1992).

Macchi, E., et al., Intracavitary Mapping: An Improved Method For Locating The Site Of Origin Of Ectopic Ventricular Beats By Means Of A Mathematical Model, *IEEE Engineering in Medicine & Biology Society 10th Annual International Conference*, pp. 0187-0188 (1988).

Macchi, E., et al., "Localization Of Ventricular Ectopic Beats From Intracavitary Potential Distributions: An Inverse Model In Terms Of Sources," *IEEE Engineering in Medicine & Biology Society 11th Annual International Conference*, pp. 0191-0192 (1989).

Masse, S., et al., "A Three-Dimensional Display For Cardiac Activation Mapping," *PACE*, vol. 14, Part I, pp. 538-545 (Apr. 1991).

Moshage, W., et al., "Biomagnetic Localization Of Ventricular Arrhythmias," *Radiology*, vol. 180, No. 3, pp. 685-692 (Sep. 1991).

Moura, L., et al., "A Microcomputer-Based Cardiac Mapping System For Recurrent Ventricular Tachycardia Surgery," *Computers in Cardiology* IEEE Computer Society Press, 0276-6547/92, pp. 431-434 (Oct. 11-14, 1992).

Pagé, P., et al., "Surgical Treatment Of Ventricular Tachycardia: Regional Cryoablation Guided By Computerized Epicardial And Endocardial Mapping," *Circulation*, vol. 80 (Suppl. I), No. 3, pp. I-124-I-134 (Sep. 1989).

Pilkington, T., et al., "Feasibility Of Estimating Endocardial Potentials From Cavity Potentials," *IEEE Ninth Annual Conference of the Engineering in Medicine and Biology Society*, IEEE, pp. 1875-1876 (1987).

Pogwizd, S. and Corr, P., "Reentrant And Nonreentrant Mechanisms Contribute To Arrhythmogenesis During Early Myocardial Ischemia: Results Using Three-Dimensional Mapping," *Circulation Research*, vol. 61, No. 3, pp. 352-371 (Sep. 1987).

Pollack, S., et al., "Intraoperative Identification Of A Radiofrequency Lesion Allowing Validation Of Catheter Mapping Of Ventricular Tachycardia With A Computerized Balloon Mapping System," *PACE*, vol. 15, pp. 854-858 (Jun. 1992).

Potratz, J., et al., "Echocardiographic Guiding Of Catheter-Electrode During Endocardial Mapping To Determine Location Of Late Fractionated Potentials In Patients With Acute Myocardial Infarction," *European Heart Journal*, vol. 12, Abstract Supplement p. 235, abstract 1242 (Aug. 1991).

Rudy, Y. and Plonsey, R., "Annotations: A Note On 'The Brody-Effect'," *J. Electrocardiology*, vol. 11, No. 1, pp. 87-90 (1978).

Rudy, Y. and Plonsey, R., "The Eccentric Spheres Model As The Basis For A Study Of The Rule Of Geometry And Inhomogeneities In Electrocardiography," *IEEE Transactions on Biomedical Engineering*, vol. BME-26, No. 7, pp. 392-399 (Jul. 1979).

Rudy, Y., et al., "The Effects Of Variations In Conductivity And Geometrical Parameters On The Electrocardiogram, Using An Eccentric Spheres Model," *Circulation Research*, vol. 44, No. 1, pp. 104-111 (Jan. 1979).

Rudy, Y. et al., "Inverse Reconstruction Of Epicardial And Endocardial Potentials: The Use Of Temporal Information," IEEE, pp. 2006-2008 (1992).

Simpson, E., et al., "Three-Dimensional Visualization Of Electrical Variables In The Ventricular Wall Of The Heart," IEEE, TH0311-1/90, pp. 190-194, (1990).

Smith, W., et al., "A Computer System for the Intraoperative Mapping of Ventricular Arrhythmias," *Computers and Biomedical Research, an International Journal*, vol. 13, No. 1, pp. 61-72 (Feb. 1980).

Smith, W. and Ideker, R., "Computer Techniques For Epicardial And Endocardial Mapping," *Progress in Cardiovascular Diseases*, vol. 26, No. 1, pp. 15-32 (Jul./Aug. 1983).

Spach, M. and Barr R., "Analysis Of Ventricular Activation And Repolarization From Intramural And Epicardial Potential Distributions For Ectopic Beats In The Intact Dog," *Circulation Research*, vol. 37, pp. 830-843 (Dec. 1975).

Stellbrink, C., et al., "Potential Of Intracardiac Ultrasonography As An Adjunct For Mapping And Ablation," *American Heart Journal*, vol. 127, No. 4, Part 2 , pp. 1095-1101 (Apr. 1994).

Taccardi, B., et al., "A New Intracavitary Probe For Detecting The Site Of Origin Of Ectopic Ventricular Beats During One Cardiac Cycle," *Circulation*, vol. 75, No. 1, pp. 272-281 (Jan. 1987).

Taccardi, B., et al., "Potential Distributions And Excitation Time Maps Recorded With High Spatial Resolution From The Entire Ventricular Surface Of Exposed Dog Hearts," *Computers in Cardiology*, IEEE Computer Society Press, 0276-6547/92, pp. 1-4 (Oct. 11-14, 1992).

Tanigawa, M., et al., "Prolonged And Fractionated Right Atrial Electrograms During Sinus Rhythm In Patients With Paroxysmal Atrial Fibrillation And Sick Sinus Node Syndrome," *Journal of the American College of Cardiology*, vol. 17, No. 2, pp. 403-408 (Feb. 1991).

Tweddell, J., et al., "Potential Mapping In Septal Tachycardia: Evaluation Of A New Intraoperative Mapping Technique," *Circulation*, vol. 80 (Suppl. I), No. 3, pp. I-97-I-108 (Sep. 1989).

Witkowski, F. and Corr P., "An Automated Simultaneous Transmural Cardiac Mapping System," *American Journal of Physiology*, vol. 247, pp. H661-H668 (1984).

Young, M., et al., "A Real-Time Data Acquisition System For The Display Of Three Dimensional Cardiac Activation Maps," *Computers in Cardiology*, IEEE Computer Society Press, 0276-6547/92, pp. 331-334 (Oct. 11-14, 1992).

Yuan, S., et al., "Localization Of Cardiac Arrhythmias: Conventional Noninvasive Methods," *International Journal of Cardiac Imaging*, vol. 7, pp. 193-205 (1991).

Kristin Clingman Spencer, "*A Feasibility Study of Determining the Position of an Intracavitary Multielectrode Probe Via Impedance Measurements,*" Department of Electrical Engineering in the Graduate School of Duke University, 1991, pp. i-vii and 1-49.

Patrick Donahoe Wolf, "*Development and Evaluation of an Algorithm to Determine Boundary Geometry and Electrode Location from Impedance Measurements,*" Department of Biomedical Engineering in the Graduate School of Duke University, 1992, pp. i-viii and 1-86.

"*New Catheter Will Find And Treat Cardiac Arrhythmias,*" WPI Journal, Summer 1993, 2 pages.

"*Quickhull Algorithm For Convex Hulls,*" ACM Transactions on Mathematical Software, vol. 22, No. 4, Dec. 1996, 1 page.

P. Mendler et al., "*Multichannel Recording Of Cardiac Potentials,*" Medical And Biological Engineering And Computing, vol. 18, No. 5, Sep. 1980, pp. 617-624.

* cited by examiner

Fig. 8a

| PATCH DRIVE | ANATOMIC LOC |
|---|---|
| Xa | LEFT SIDE |
| Xb | RIGHT SIDE |
| Ya | BACK |
| Yb | CHEST |
| Za | NECK |
| Zb | LEFT LEG |

Fig. 8c $$\text{Eqn 1} \quad \sum_{i=1}^{N}\left[\text{Ems}_i - \sum_{k=0}^{5} R_{ki} * W_k\right]^2$$

Fig. 8d $$\text{Eqn 2} \quad ER_i = E_i - \left(\sum_{k=0}^{5} R_{ki} * W_k\right)$$

METHOD AND APPARATUS FOR CATHETER NAVIGATION AND LOCATION AND MAPPING IN THE HEART

CROSS-REFERENCE TO RELATED CASES

The present application claims the benefit of U.S. Provisional Patent Application 60/461,004 filed Apr. 7, 2003, which is incorporated by reference herein. The present Application is also a Continuation in Part of U.S. patent application Ser. No. 09/107,371 filed Jun. 30, 1998. Each application is incorporated by reference in its entirety herein.

FIELD OF THE INVENTION

The present invention relates generally to a computer based medical system that can be used to position and navigate electrophysiology catheters and ablation catheters inside the heart of a patient. The catheters are used to create an image of the interior of the heart, and electrophysiology information collected from the catheters is presented to a physician user to guide a therapy or diagnosis.

BACKGROUND OF THE INVENTION

Wittkampf in his U.S. Pat. Nos. 5,697,377 and 5,983,126, discloses a system for determining the position or location of a catheter in the heart. These patents are incorporated by reference in its entirety herein.

In the Wittkampf system current pulses are applied to orthogonally placed patch electrodes placed on the surface of the patient. These patches are used to create axes specific electric fields inside the patient. The patents teach the delivery of small amplitude low current pulses supplied continuously at three different frequencies, one on each axis. Any measurement electrode placed in these electric fields (for example in the heart) experiences voltages depending on its location between the various patches or surface electrodes on each axis. The voltage on the measurement electrode in the field when referred to a stable positional reference electrode indicates the position of the measurement electrode in the heart with respect to that reference. The three voltages give rise to a location of the measurement electrode in "three space".

Although the Wittkampf system is both safe and effective there are several sources of error that result in errors in position or electrode location. Principle among these is the respiration artifact. For these reasons there is a need for improved location and navigation methods to improve the functionality of the system for the physician.

SUMMARY OF THE INVENTION

The present invention is disclosed in the context of a system for collecting and displaying "heart" data to a physician. This is an illustrative and not limiting example of the use of the methodologies. For example it should be clear that the techniques can be used guide the delivery of general surgical devices into the body or to guide and position drug delivery devices among other applications.

In the present invention, several improved location and navigation methodologies are presented and these are used to determine more accurately the location in space of a multitude of electrodes located on catheters inserted into any heart chamber. This improved location data is used to create a geometric representation of the whole heart chamber. In addition, the improved methodologies allow for the collection and presentation of electro physiologic (EP) data to the physician. This "activation mapping" aspect of the system allows the system to present EP data and catheter location data on an accurate representation of the heart. This improves the functionality of the system for both diagnosis and intervention. A typical use would include the use of ablation catheters to find the origin of a cardiac arrhythmia and then to treat it with RF energy to ablate tissue.

In the prior art and for many years physicians have measured electrical potentials on the interior walls of the heart with electrodes in contact with that tissue. In general the time course of electrical impulse at each electrode is displayed in a "timing window". This plot of voltage against time is displayed and the physician looks at this data and visually determines the "site" or location of earliest activation. That is the physician determines which of the electrodes is closest to the ectopic focus or other origin of depolarization signals in the heart.

In the present invention multiple electrodes are swept over the surface of the heart. Each electrode is "located" in space using the location algorithm and the voltage present on that electrode is measured and stored. The timing information related to the measured voltage and a fiducial electrographic event such as the R-wave is also stored by the system.

These measurements are made continuously in a beating heart and the measurements are made without regard to the specific cardiac phase. To present this information to a physician the electrode location information is used to project a measurement point onto the geometry created by the roving catheter. The "timing" information or the voltage "magnitude" information is interpreted as a false color that is presented and projected to a point on the heart surface geometry.

It should be recognized and understood that the electrophysiology data or activation mapping data can change during the heartbeat. As a consequence a typical display would include animation of the EP data showing the passage of electrographic wave fronts over the surface of the heart as represented by the geometry.

Several related methods are taught including:

Respiration Compensation

A method of compensation for respiration is disclosed. The compensated signal allows for greater location accuracy of electrodes in the heart. In brief the respiration motion artifact is measured and subtracted from the measurement or roving electrode position data to improve accuracy.

Virtual Reference Generation

A method of generating a non physical reference position which permits the operation of the system without a fixed physical reference electrode attached to the heart. This virtual reference is a benefit to the patient and a significant improvement for the physician.

Geometry Capture

The improved location methodologies allow for the collection of location data from one or more catheter electrodes all during the heart contraction cycle and without keeping track of the phase of the heart. The data is "reduced" to create a "shell" which represents the shape of the heart chamber swept by the electrodes.

EP Mapping

One or more catheters having one or more electrodes are moved around in the heart chamber. Throughout this process the electrodes are in contact with the heart wall. The electrical potentials on these electrodes are measured and there location in space noted. The electrical data is then projected on the geometry as an activation map. The activation mapping methodology permits the display of peak to peak voltages at various locations on the geometry. The activation mapping methodology permits the display of timing relationships between the measured voltages and a fiducial timing reference at various locations on the geometry.

BRIEF DESCRIPTION OF THE DRAWINGS

The embodiments of the invention shown are illustrative and various modifications may be made to the invention without departing from the scope of the invention. Throughout the figures identical reference numerals refer to equivalent structure, wherein:

FIG. 8 is a figure showing representative expressions for calculations;

DETAILED DESCRIPTION OF THE INVENTION

System Level Overview and Basic Location Methodology

Figure 1:
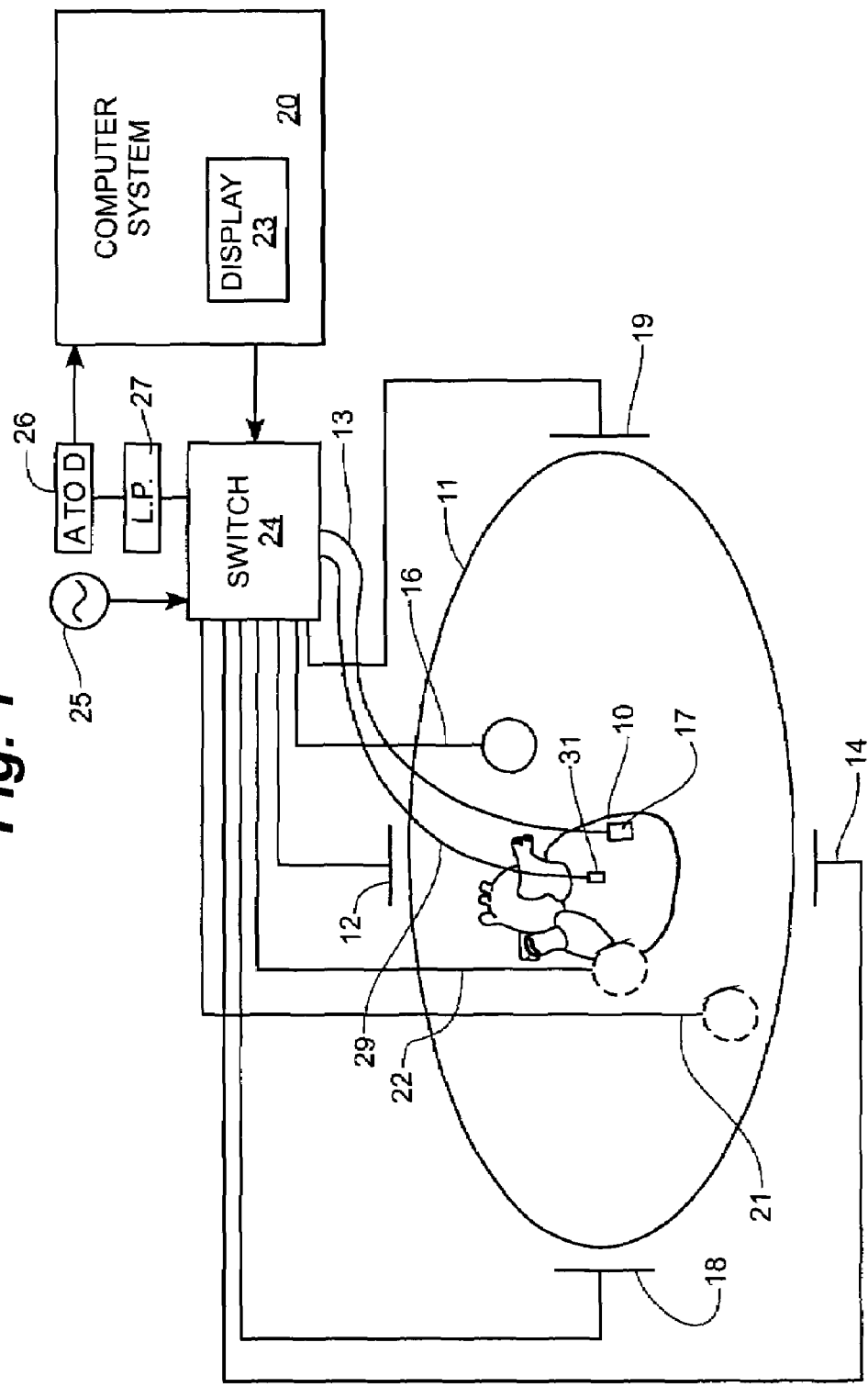
FIG. 1 is a schematic overview of the system.

FIG. 1 shows a system level diagram in schematic form. The patient 11 is depicted as an oval for clarity. Three sets of surface electrodes are shown as 18,19 along a Y-axis; as 12,14 along an X-axis; and 16, 22 along a Z-axis. Patch electrode 16 is shown on the surface closest the observer and patch 22 is shown in outline form to show the placement on the back of patient 11. An additional patch electrode called a "belly" patch is also seen in the figure as patch electrode 21. Each patch electrode is independently connected to a multiplex switch 24. The heart 10 lies between these various sets of patch electrodes. Also seen in this figure is a representative catheter 13 having a single distal electrode 17 for clarity. This distal electrode 17 is called the "roving electrode" or "measurement electrode" throughout the specification. Typically multiple electrodes on each catheter will be used. A fixed reference electrode 31 attached to a heart wall is also seen in the figure on an independent catheter 29. For calibration purposes this electrode 31 is known to be stationary on the heart.

It should also be appreciated that in use the patient will have most or all of the conventional 12 leads ECG system in place as well and this ECG information is available to the system although not illustrated in the figure.

Each patch electrode is coupled to the switch 24 and pairs of electrodes are selected by software running on computer 20, which couples the patches to the signal generator 25. A pair of electrodes, for example 18 and 19, are excited by the signal generator 25 and they generate a field in the body of the patient 11 and the heart 10. During the delivery of the current pulse the remaining patch electrodes are referenced to the belly patch 21 and the voltages impressed on these remaining electrodes are measured by the A to D converter 26. Suitable lowpass filtering of the digital data is subsequently performed in software to remove electronic noise and cardiac motion artifact after suitable low pass filtering in filter 27. In this fashion the surface patch electrodes are divided into driven and non-driven electrode sets. While a pair of electrodes a driven by the current generator 25 the remaining non-driven electrodes are used a references to synthesize the orthogonal drive axes.

The belly patch electrode 21 is seen in the figure is an alternative to a fixed intra-cardiac electrode 31. In many instances a coronary sinus electrode or other fixed electrode in the heart can be used as a reference for measuring voltages and displacements. All of the raw patch voltage data is measured by the A to D converter 26 and stored in the computer under the direction of software. This electrode excitation process occurs rapidly and sequentially as alternate sets of patch electrodes are selected and the remaining members of the set are used to measure voltages. This collection of voltage measurements is referred to herein as the "patch data set". The software has access to each individual voltage measurement made at each patch during each excitation of each pair of electrodes.

The raw patch data is used to determine the "raw" location in three space (X,Y,Z) of the electrodes in side the heart such as the roving electrode 17. The patch data is also used to create a respiration compensation value used to improve the raw location data for the electrode locations.

If the roving electrode 17 is swept around in the heart chamber while the heart is beating a large number of electrode locations are collected. These data points are taken at all stages of the heart beat and without regard to the cardiac phase. Since the heart changes shape during contraction only a small number of the point represent the maximum heart volume. By selecting the most exterior points it is possible to create a "shell" representing the shape of the heart. The location attribute of the electrodes within the heart are measured while the electric field is impressed on the heart by the surface patch electrodes.

Figure 2:
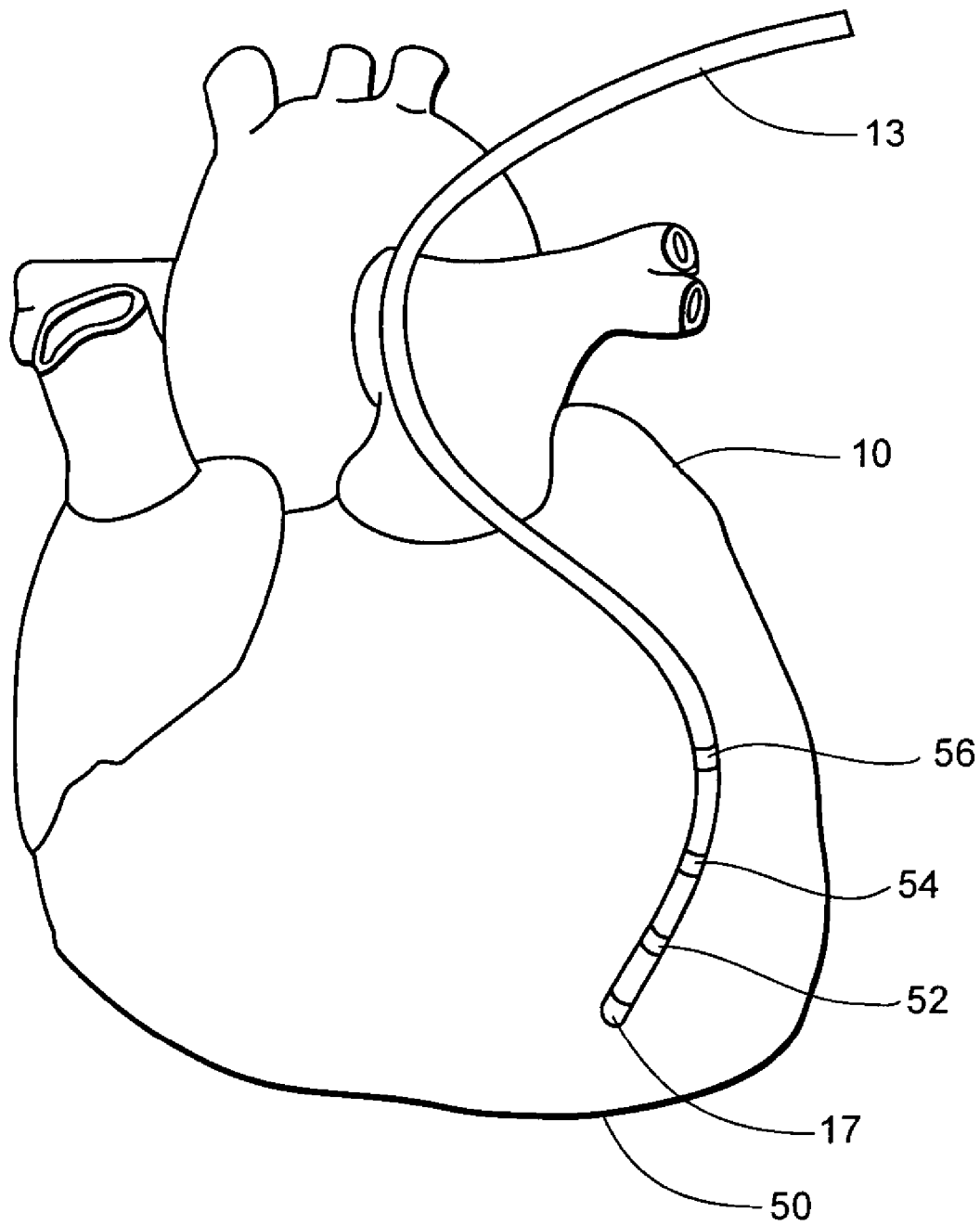
FIG. 2 is a schematic view of a catheter in a heart chamber.

FIG. 2 shows a catheter 13 which may be a conventional EP catheter in the heart 10. In the figure it 13 is shown in the left ventricle 50. The catheter 13 has additional electrodes 52 54 and 56. Since these electrodes lie in the heart the location process detects their location in the heart. While they lie on the surface and when the current source 25 is "off", each electrode can be used to measure the voltage on the heart surface. The magnitude of this voltage as well as its timing relationship of the signal with respect to the heartbeat events are measured and presented to the cardiologist through the display 23. The peak to peak voltage measured at a particular location on the heart wall shows areas of diminished conductivity and may reflect an infracted region of the heart. The timing relationship data are typically displayed as "isochrones". In essence regions that receive the depolarization waveform at the same time are shown in the same false color or gray scale.

Figure 3:
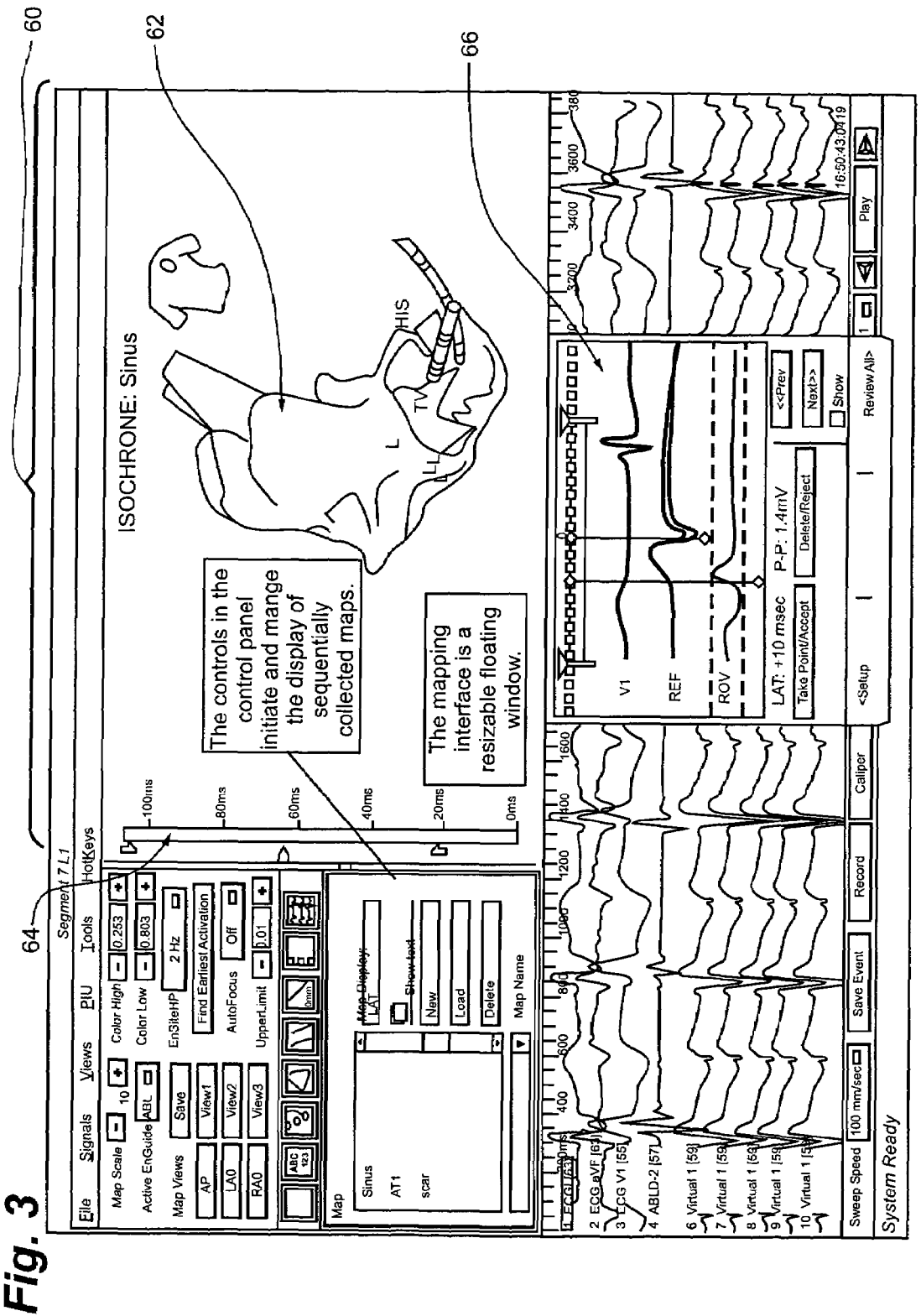
FIG. 3 is a display screen showing operation and interaction with the overall system.

FIG. 3 shows an illustrative computer display from the computer system 20. The display 23 is used to show data to the physician user and to present certain options that allow the user to tailor system configuration for a particular use. It should be noted that the contents on the display can be easily modified and the specific data presented in illustrative and not limiting of the invention. An image panel 60 shows a geometry of the heart chamber 62 which shows "isochrones" in false color which is shown in grayscale in the figure with guide bar 64. In this image the improved location methodology has been used with a roving catheter to create a chamber representation that is displayed as a smoothed contoured image.

The guide bar 64 is graduated in milliseconds and it shows the assignment of time relationship for the false color image in the geometry. The relationship between the false color on the geometry image 62 and the guide bar is defined by interaction with the user in panel 66 best seen in FIG. 4.

Figure 4:
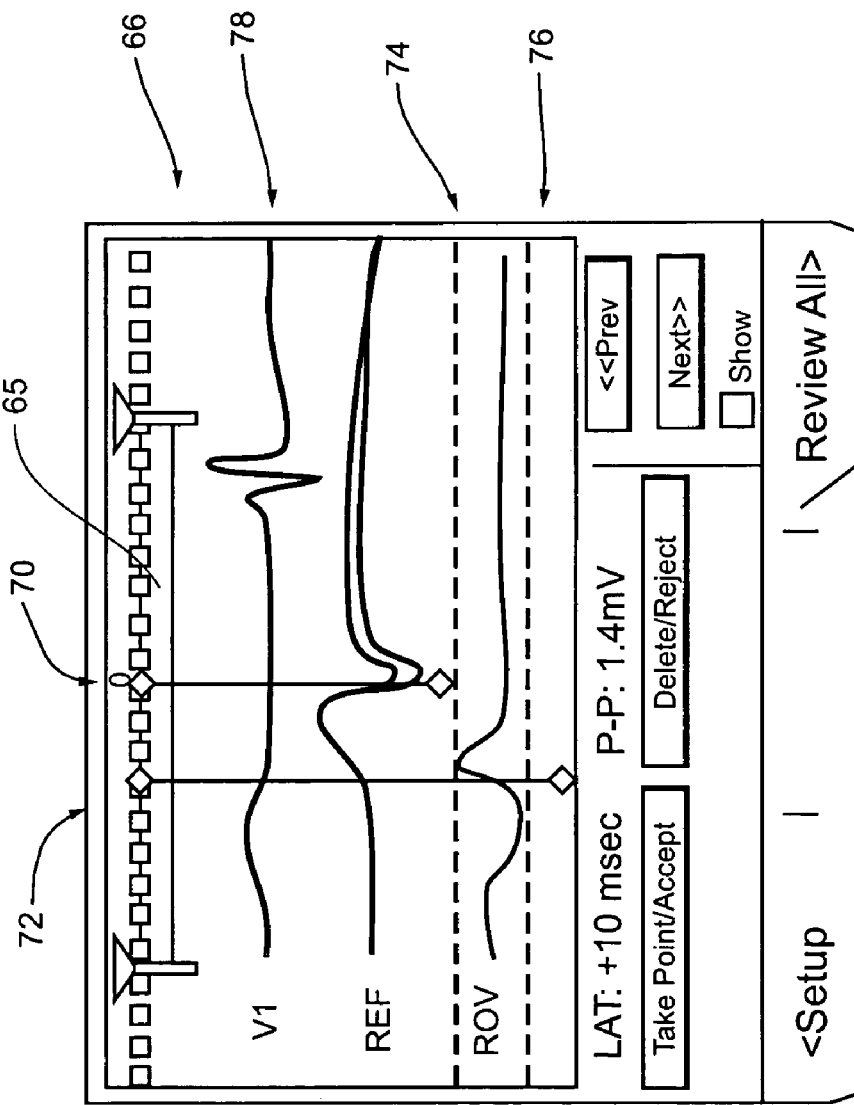
FIG. 4 is a is a display screen showing operation and interaction with a portion of the system.

FIG. 4 is an enlargement of panel 66 of FIG. 3. The panel 66 represents the timing information used to generate the isochrones seen on geometry 62. In general, a fiducial point is selected as the "zero" time. In the figure the inflection point 70 of a voltage appearing on a reference electrode is used as the primary timing point for the creation of isochrones. This voltage may be acquired from either the virtual reference or a physical reference such as electrode 31 seen in FIG. 1. This voltage tracing in the figure is labeled "REF" on FIG. 4. The roving electrode signal is seen on FIG. 4 and it is labeled "ROV" in the figure. The inflection point of this voltage signal is shown at 72. The color guide bar 65 shows the assignment of color or grayscale tone for the timing relationship seen between inflections 70 and 72.

Also shown on panel 66 of FIG. 4, is the amplitude of the signal present on the roving electrode. Note that it lies between two adjustable bands 74 and 76. These bands are used to set selection criteria for the peak to peak voltage of the signal. In practice regions of the heart with low peak-to-peak voltage are the result of infarcted tissue and the ability to convert voltage to grayscale or false color allows identification of the regions that are infracted or ischemic.

For completeness in description the tracing 78 labeled "V1" in FIG. 4 is a reference electrode on the surface of the patient in the conventional 12 lead ECG setup. This reference orients the physician to the same events detected on the surface of the patient.

In summary the basic software process proceeds stepwise by first selecting a set of electrodes and then driving them with current pulses. While the current pulses are being delivered the voltages on several of the other remaining surface electrodes and intracavitary electrodes are measured and stored. At this point it is preferred but not required to compensate these measured values with coefficients taken from the respiration compensation process.

It is this process that collects the various data points associated with multiple endocardial electrode locations. Each point in this set has coordinates in space. In general several dozen points are collected. A larger data set results in a more complex and higher resolution representation of the heart however, it is computationally more expensive. The raw location data is corrected for respiration and other artifacts and then a geometry process is started. In this process the exterior most location points in the data are used to create a shape. The preferred surface is a convex hull using standard algorithms such as Qhull. This surface is then resampled over a more uniform grid and interpolated to give a reasonably smooth surface stored as a "geometry" for presentation to the physician. The algorithm is used to compute the convex hull shape is well known and it is one of many potential algorithms suitable for use in implementing the invention. This shape estimates the boundary of the interior of the heart from the set of points. The process then proceeds to resampled the convex hull on a regular grid of points in physical space. By resampling the computed hull shape on the regular grid, a larger set of points is generated. Most significantly this enlarged set of points ensures that computational points are available along the length of each edge of the hull. The next process uses an algorithm for smoothing the convex hull shape. This process forms a mathematically differentiable shape approximating the physiologic shape of the heart chamber. Any of a number of interpolation processes can be adopted to implement this portion of the process. The final process causes the model to exit to a display routine or other process where the computed shape is used for further analysis.

This geometry surface is also used a display surface to present the activation maps. This is also the surface that the EP data is project on.

As described the EP catheters are moved over the surface of the heart and while in motion they detect the electrical activation of the heart or EP signals on the surface of the heart. During each measurement the real time location of the catheter electrode is noted along with the value of the EP voltage or signal. Since this data is not taken with the location data used to create the geometry a projection process is used to place the electrical information on the nearest heart surfaces represented by the geometry. The preferred implementation is to select two close points or locations in the EP data set and to "drop" a perpendicular to the "nearest" surface point on the geometric surface. This new point is used as the "location" for the presentation of EP data in the images presented to the physician.

Respiration Compensation Methodology

The basic location methodology described above provides a first order indication of the location of a roving or other catheter electrode within the heart chamber. However the primary artifact to mitigate in the basic location methodology is due to patient ventilation or breathing. For example, with reference to the belly patch 21 reference, error displacements exceeding two centimeters due to breathing have been noted in the left atrium experiments in human data as measured with a with a roving catheter electrode 17. The same data when referenced to a fixed electrode (coronary sinus electrode) the measured error displacement still exceed about one centimeter. In these experiments the data is collected with a 0.25 Hz low pass filter setting. Using higher low pass settings (necessary for geometry creation) makes the situation even worse, plus it allows a significant stroke signal component that will be due both to actual displacement during contraction, as well as impedance changes due to blood ejection. For these reasons a simple filtering algorithm is inadequate to compensate for respiration.

Figure 5:
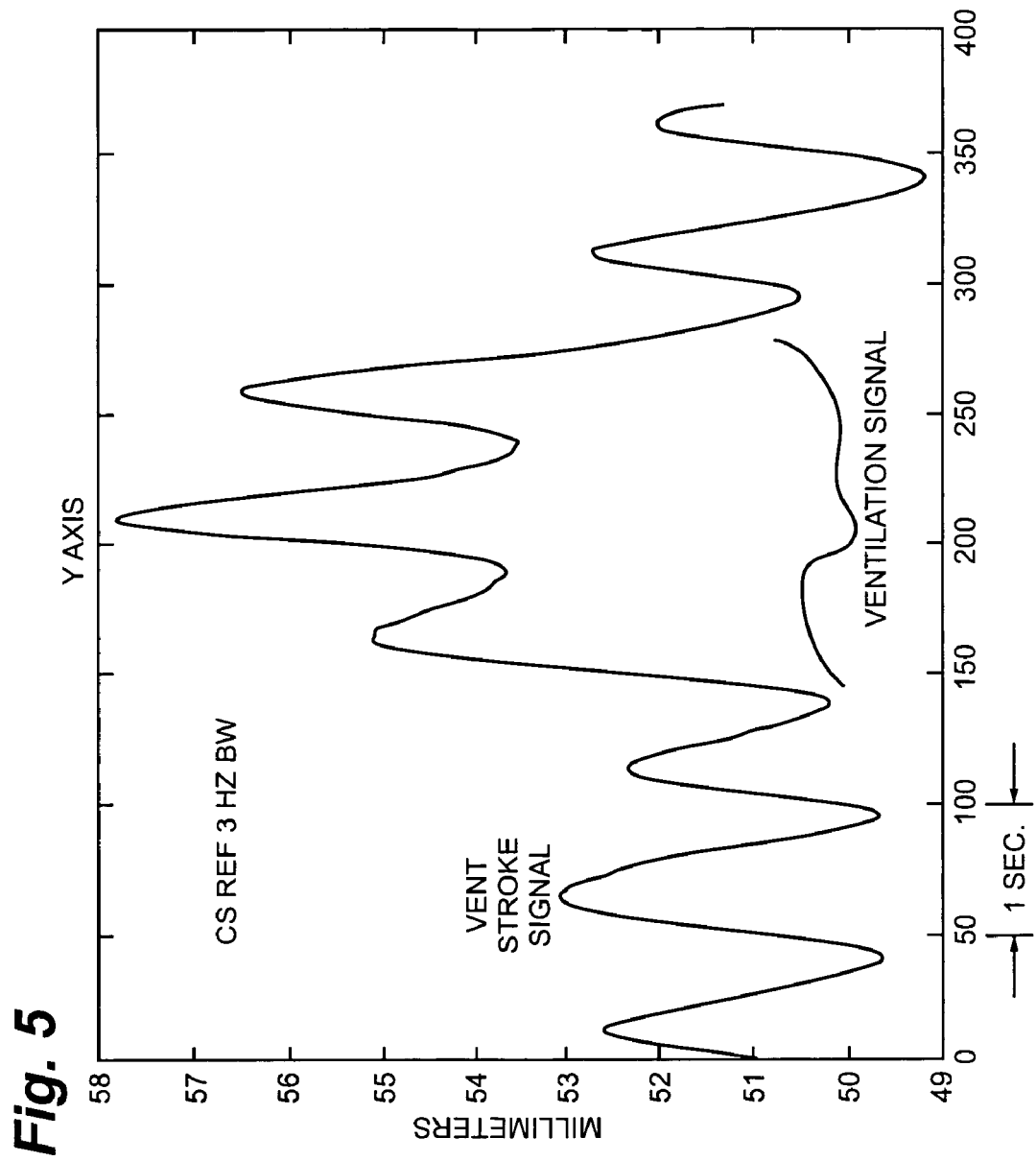
FIG. 5 is a tracing of data showing respiration artifacts.
Figure 6:
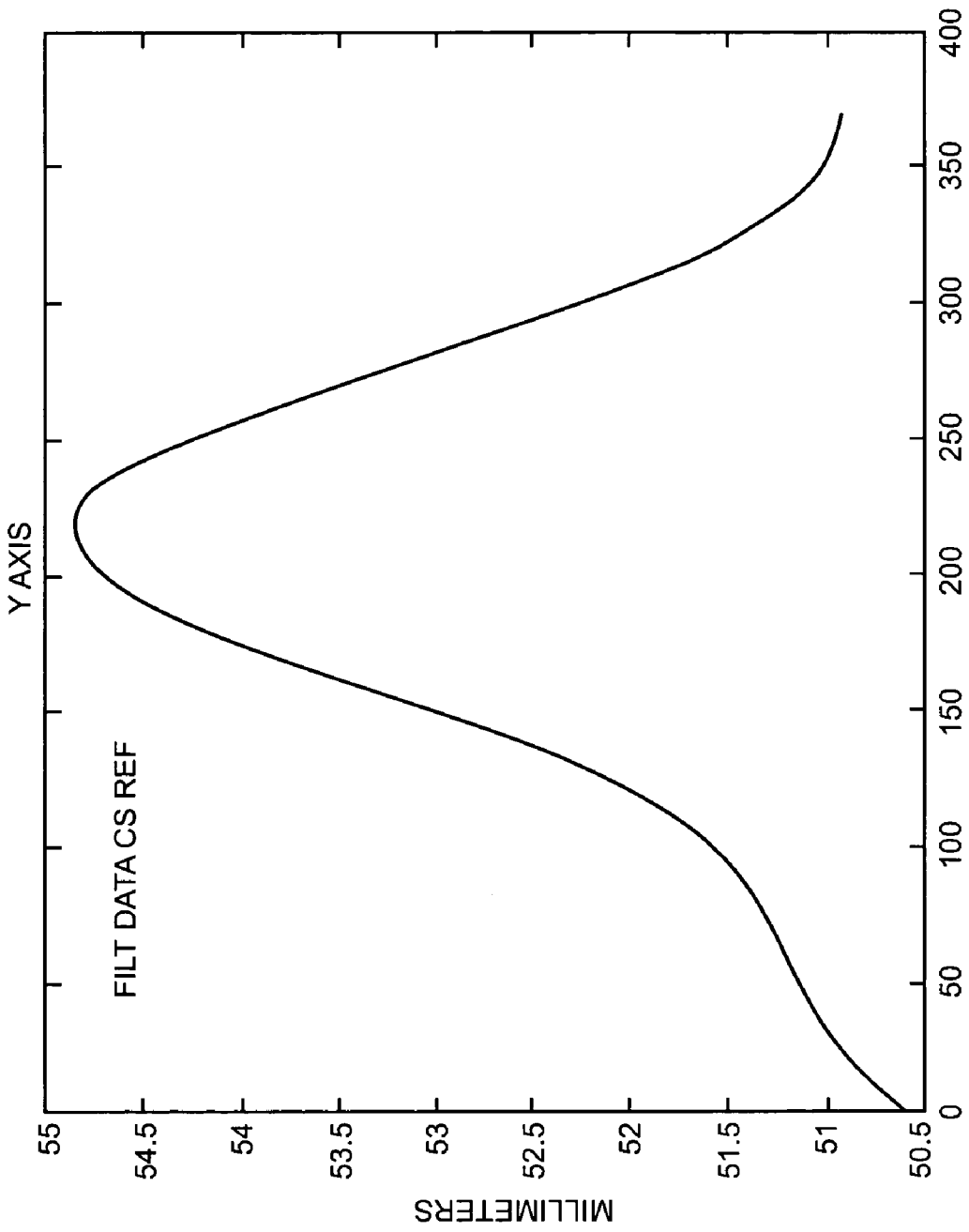
FIG. 6 is a tracing of data showing the elimination of respiration artifacts.
Figure 7A:
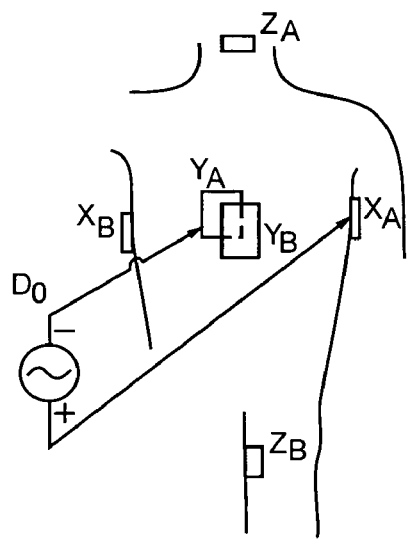
FIG. 7 is a schematic showing the patch orientations and nomenclature.
Figure 7B:
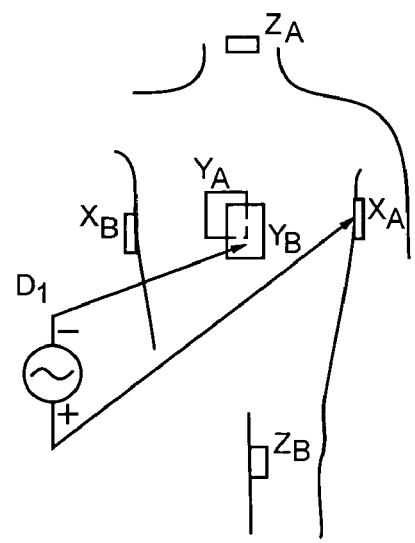
Figure 7C:
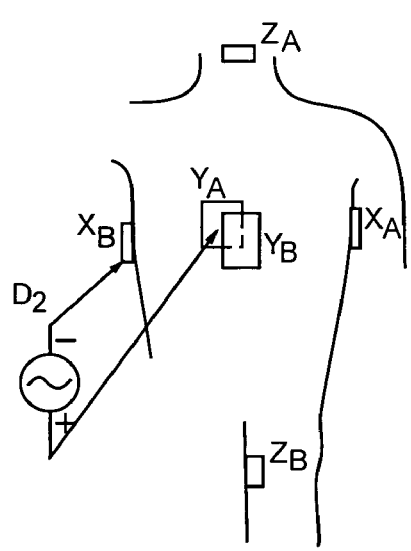
Figure 7D:
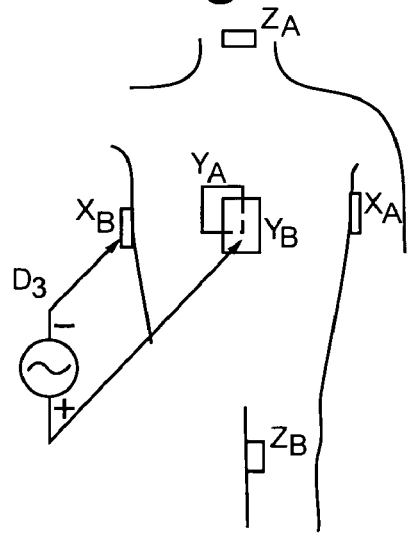

FIG. 5 shows experimental data taken under the conditions described above. In the figure one sees an example of both ventilatory and stroke signal modulation of a roving electrode 17 tracked electrode using a 1.0 Hz setting using the basic location methodology. FIG. 6 shows the same data with the 0.25 Hz low pass filter 27 setting. In general it is preferred to use a 0.25 Hz setting for low pass filter 27 for collecting EP data from the patient and the 1 Hz setting to collect geometry information. In the figures, the abscissa is "samples" and there are 50 samples to 1 second. There are several causes of ventilation modulation of the catheter electrode position in the system.

First, there are changes in the current paths from the axes drives when the lungs fill with air. This alteration of path changes the measurement. This changes the potential between the tracked or roving electrode 17 and the reference electrode. Respiration also moves the patches apart and this displacement of the patch drive electrodes with respect to the heart changes the measurement. Secondly, the resistivity of blood returning to the heart from the lungs is altered following inspiration. A compressive effect of filling lungs on the heart may cause some displacement the catheters themselves may actually move due to stretching or tension upon inspiration.

In addition with the belly patch 21, or another body surface patch as reference, there may be displacement of the patch sense electrode with respect to the heart.

Because the frequency components of ventilation can be so low (approximately 0.1-0.2 Hz) only very heavy filtering would adequately remove artifacts but this would result in an unacceptably slow responding system. For this reason filtering alone does not improve the system.

Fixed Electrode Reference

The large ventilatory displacements seen with a body surface reference electrodes is evident in the Medtronic Localisa™ system which is commercially available and similar to the Wittkampf system described in the incorporated reference. This system uses a fixed intra-cardiac electrode reference catheter which is usually a screw in tip pacing lead. A screw in tip is added expense and risk for the patient. An alternative coronary sinus catheter or other fixed reference may be substituted but these may move during the study, rendering a navigation map inaccurate. Even with a "fixed cardiac reference" the ventilation artifact remains problematic.

Virtual Reference

Two discrete, independent but complementary methods are discussed herein to address the problem of a surface electrode reference: the virtual reference VRV and a method of respiration compensation or RCV. While the virtual reference has less artifact than just using a single belly patch, even greater suppression of respiration artifact can be achieved using subsequent respiration compensation. Or, if an intra-cardiac reference is desired and is available, the respiration compensation method may still be applied using intra-cardiac reference.

The key objective of the virtual reference is to facilitate the basic location methodology without requiring a separate stable intra-cardiac reference electrode and catheter.

Potentials on any of the six electrodes are acquired for all samples except when an electrode is driven. Sampling while an electrode is acting as a source or sink is explicitly avoided, as the potential during this time, at the electrode will include the electrode impedance and the effects of high local current density.

FIG. 8 table 1 defines the representative designations of electrode configuration discussed below.

Drive Axes Synthesis

Before discussing the virtual reference in detail, and with reference to FIG. 8, an overview of the current pulse drive method will be described. For any desired axis, the potentials on an intra-cardiac electrode resulting from a pre-determined set of drive (source->sink) configurations are combined algebraically to yield the same effective potential as would be obtained by simply driving a uniform current along the desired axis. For convention, we'll list the source and sink configuration with an arrow, and following that, an underscore to indicate a sense electrode (again, all electrical sensing is done with respect to electrical common, or in our case the "belly patch"). Thus sourcing from A and sinking to B, while sensing at C would be denoted A->B_C. If one inverts the drive sense, the resulting potentials measured will be the same as that obtained by negating the non-inverted drive configuration. In other words, the potential due to a dipole driving from electrodes A to C is equivalent to subtracting the potential due to dipole A to B and subtracting dipole C to B. The advantage of decomposing the problem into multiple dipoles instead of merely driving the three axes directly is that additional data is available for respiration compensation as described in that section. We will describe the X axis in detail; the Y and Z axes are identical in principle, and the treatment of each axis is completely independent of the others.

The drive configurations that comprise the data used to generate the X axis are shown in FIG. 7. For example, D0 is the drive configuration where the current source is switched to deliver positive current from electrode XA, and sink the current to YA. (Each of these configurations is multiplexed at a sampling rate of about 100 times per second.)

The net X axis potential on a given sense electrode, "E" in the heart chamber, using the principle of reciprocity but essentially equivalent to Wittkampf's method, is obtained by sampling the electrode potential obtained while driving each of the 4 drive configurations, and combining them arithmetically.

Virtual Reference Computation

As previously discussed it is useful to place an electrode in the heart attached to the heart wall to operate as a location reference for measuring the location of other catheters. This can be done with a screw in type pacing lead or a pacing type lead placed in the coronary sinus. Although this is a useful expedient, the presence of additional catheters in the chamber is always unwelcome during ablation procedures and the like. One aspect of the present invention is the creation of the virtual reference, which eliminates the need for a fixed physical reference electrode. The virtual reference is a computed value that is applied to the measured values of location electrode data to simulate or emulate the position of a fixed lead. The process proceeds as follows:

The data from any four of the six patches (the system electrical reference being a seventh "belly patch") is available whenever a pair of patches is driven. (Again, the sensed data from the driven patches is not used.)

While other choices may be contemplated, the preferred method for computing the virtual reference potential for the X axis is nominally the midpoint of the chest (YB) and back (YA) patches, since each of them is used with exactly ½ of the weight of the normal electrode Ex, described above.

The net X axis potential for electrode E is solved for by subtracting the value of the X axis virtual electrode value from the measured X axis value. A similar process can be used to find the other three space values for the roving or other electrode.

Therefore in summary, a set of patch electrodes is placed on the skin or surface of the patient. Two of these are selected to source current with respect to a ground reference, while the remaining electrodes measure voltage with respect to the ground reference. An electrode placed in the heart exposed to the field from the current pulse is also measured with respect to ground. In practice the catheters within the heart may contain multiple electrodes and each electrode ring potential is measured. Preferably at least one electrode is fixed to the interior surface of the heart and forms a fixed reference, which is also measured with respect to ground. The patch electrode data set, the internal electrode data set and the virtual electrode data set are all used to determine the location of the electrodes within the heart. After the voltage measurements are made a different pair of surface electrodes is excited by the current source and the voltage measurement process of the remaining patch electrodes and interior electrodes takes place. The sequence occurs rapidly on the order of 30 kHz. To a first approximation the voltage on the electrodes within the heart bears a linear relationship with position between the patch electrodes that establish the field within the heart. Although useful location information can be acquired with a linear model, it is preferable to compensate for respiration which varies rhythmically as the patient breathes and non-linearity within the bio-impedance of the body. In a preferred method correction factors are applied to the raw location information to improve the accuracy of the location value.

Application of Respiration Compensation

As the patient breathes the lung's volume changes and the impedance between patch electrodes varies not only as a function of electrode position but as respiration as well. Consequently it alters the perceived location of the electrode. Although the displacement or inaccuracies associated with respiration are small, it is important to remove them if possible because the ablation location positioning can be critical to achieve the therapeutic result desired by the physician.

A weighting optimization is used that requires the acquisition of data at a stable catheter electrode position for a long enough epoch to ensure that a breath was acquired (10 seconds is adequate). During this "ventilation nulling" or determination of weights, the error term (i.e. that which is to be minimized) is the perturbation of the position of "E".

A 10-second buffer of data from a stable electrode "E" is acquired and the algebra described in the previous section is applied. This yields a time vector of data. For respiration compensation, the choice of reference is immaterial: in other words the electrode data may have the virtual reference applied (Enet), another intra-cardiac reference, or it may merely be referred to the electrical (belly patch) reference.

The gist of the respiration compensation method requires recognizing two facts: the electrode that is "apparently" moving (due to the above-cited ventilatory mechanisms) is known to be essentially stable; and a related component of the movement artifact is present on the un-driven patch electrodes.

Six sets of patch data at each time are acquired as follows. First, the patch data is high pass filtered with a corner frequency in the neighborhood of 0.01 Hz. This removes DC information from the patch data, since we're only interested in time varying (respiration) artifact above this frequency.

Again, considering the X axis only, a vector of patch data designated "R" is comprised of the following, for a given time sample. Note that the four drive dipoles (D0-D3) are used, and sampling from all six patches is obtained. The table B in FIG. 8 shows a representative calculation.

Respiration Compensation Algorithm

Consider now, a set of sampled data from an acquired 10 second epoch where the electrode "E" was essentially stationary. Since the data from intra-cardiac electrode data E(i) ("i" indicates time sample number) is by user enforcement, from an anatomically stable site, we subtract the mean of the vector from the samples, at which point we're left a noise vector, or variation about zero. Denote this Ems(i). Ideally we would like this to be zero. The respiration compensation weights, W(0-5) are determined by minimizing the expression which is a linear least squares problem, amenable to singular value decomposition or other linear solution methods. The representative expression is seen as expression "C" in FIG. 8. In other words, in the linear system solution, a set of six weights (W) is determined, such that when each weight is multiplied by its respective R vector as defined above, and the results are summed, the inner sum is optimally close to the noise (respiration artifact) across the sampled epoch.

Once determined, the compensation is applied by merely subtracting in real time sample the weighted sum of the R vectors derived from the patch data, yielding a net compensated sample Eri defined in FIG. 8 table "D" and the Y and Z axis weights may be determined in an analogous manner.

Data Over-fitting & Mitigation

Initial results revealed that the above solution was prone to "over-fitting" of the data, meaning that relatively large weights would result from the optimization, with very small residuals. This weighting, however, would generalize poorly to other test data from the same patient. Note that after filtering, the NavX data has very low bandwidth, and after DC removal, consists primarily of the ventilation artifact, assuming a stable anatomic location. The approximating power of the respiration compensation data to match the normal electrode data with optimal weighting is very high. The over-fitting problem was solved by adding a small amount (0.012 ohms RMS) of noise to the data prior to solving for the weights.

It was also found that best results are obtained by concatenating more than one epoch of data from the patient, each individually from stable locations. Mean subtraction of the intra-cardiac electrode data applied separately to each epoch removes the "location" information, again leaving the noise components in the data. Given the approximating power of the method, the ability to deal with ventilation impact across the chamber is enhanced with a greater representation of optimizing data.

Stability of the input data is important; if the catheter is moved or changes position significantly during the epoch acquisition, the algorithm will attempt to determine weights to nullify that displacement.

Method & Algorithm Summary

The electrode on an "active" or roving intra-cardiac catheter is designated via software. Ideally this would be the ablation tip electrode 17 or the first ring electrode.

The clinician parks the catheter in an anatomically stable site as indicated by fluoroscopy. Next the -physician will interact with the display 23 by clicking a GUI button to acquire a 10-second prospective buffer. The user is asked for confirmation to accept the acquisition. The clinician is asked to move the catheter to one more stable site in the chamber, ideally far removed from the first, and a second 10-second buffer is acquired. The clinician is given the option to quit and apply, or acquire additional stable sites.

In software the following events occur:

The electrode data for each separate acquisition (epoch) is mean subtracted.

The epochs are concatenated.

12 milliohms of Gaussian noise is added to the electrode channel data and the 6 patch channels.

Equation 1 or expression "C" on FIG. 8 as configured for each axis is applied to determine the weights for each axis.

From this point forward, the basic location computation incorporates weighted subtraction per equation 2 or expression "D" on FIG. 8.

Geometry Generation

As discussed above a specific electrode called the roving electrode 17 is placed on a roving catheter which is swept around the interior of the heart by the physician. The location of this roving electrode is monitored continuously and without regard to the heart phase. The improved location process previously described is used to collect the data points. As a result, the multitude of electrode locations taken over time form a "cloud" of points. A mathematical algorithm such as a convex hull algorithm is used to construct a surface surround this cloud of electrodes and this algorithm or process "prefers" the most exterior points so that a shell is formed around the cloud. It is generally assumed that the most exterior points occurred during distally while the more interior points most likely occurred during systole. The quality of the shell model or its accuracy depends upon both the accuracy of the location algorithm and the number of points collected. The exterior shell is referred to throughout the specification as the geometry of the chamber.

Figure 9:
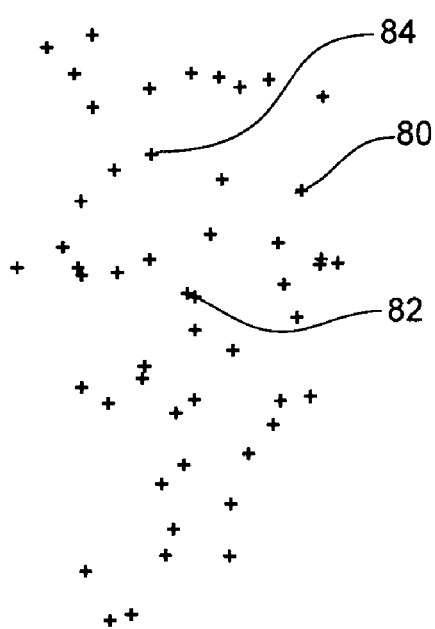
FIG. 9 is a schematic diagram of a collection of data points developed from the basic location methodology.

FIG. 9 is a graphical representation of the results of sequential measurements made in the heart. This figure is intended to show a three dimensional cloud of data points representing the location data improved with the compensation methodology. For purposes of this illustration all the data points for all of the discrete measurement periods are displayed together, with representative data points 80, 82 and 84 identified in the figure.

Figure 10:
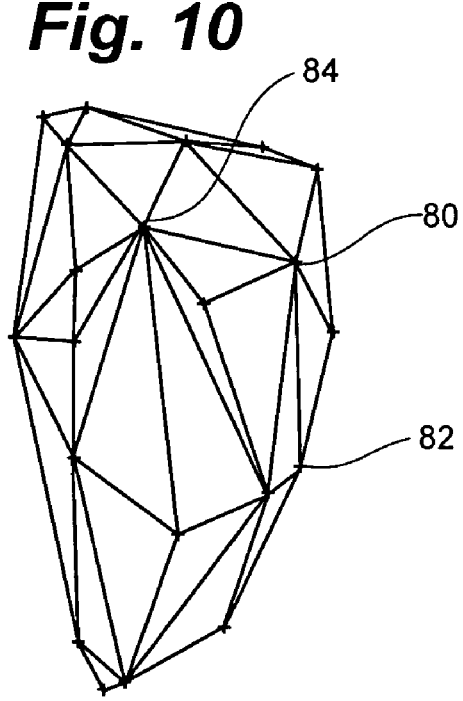
FIG. 10 is a schematic diagram of a computed convex hull heart surface.

FIG. 10 is a convex hull shape computed for the cloud of points represented in FIG. 9. This surface represents connections between the most exterior points in the data set. Usually the hull is composed of triangular panels. Convex hull algorithms are well known and publicly available software packages are available to perform this calculation, such as QHULL.

Figure 11:
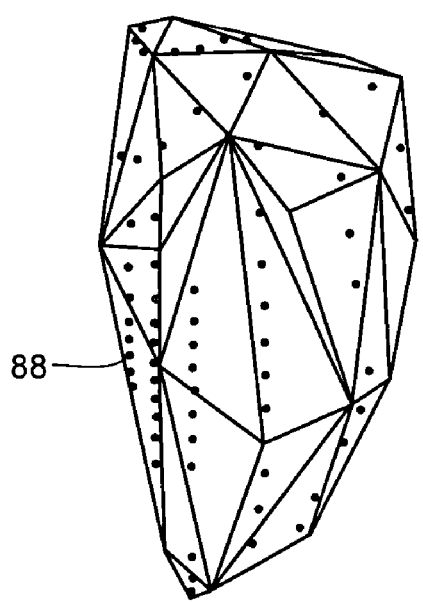
FIG. 11 is a schematic diagram of a re-sampled convex hull surface.

FIG. 11 shows the resampling process carried out on a regular grid to increase the number of points for further computation. The resampling process interpolates between vertices on the exterior of the polygon. In essence intermediate points are defined within each facet of the hull or polyhedron as represented by data point 88. Although the resampling process creates "fictitious" interpolated points these points are useful in the smoothing operation shown in FIG. 12.

Figure 12:
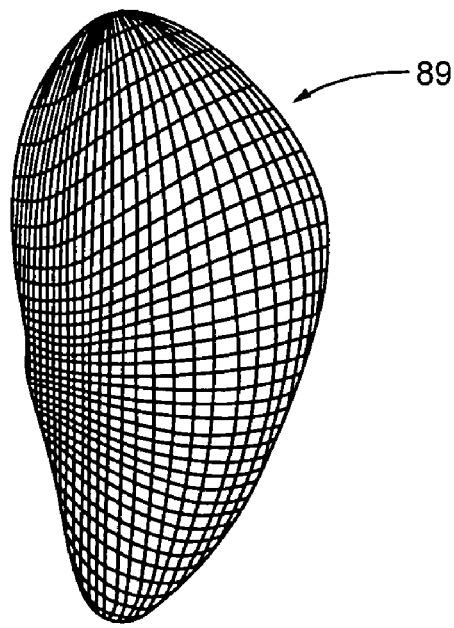
FIG. 12 is a smoothed computed heart surface.

FIG. 12 shows a smoothed shape 89 which represents a more realistic contour than the polyhedron. This surface is computed by fitting smooth curves to the enlarged or enhanced data set generated by the resampling process. Conventional smoothing algorithms are used corresponding to a least squares fit. This process yields a mathematically differentiable surface.

Although there are numerous ways to use the sequential data, one useful technique is to construct a normal from the surface and to note the point at which it intersects a superimposed hull of greater volume. The distance between the two surfaces is calculated along the direction of the normal and this distance measurement is used to compute velocity and acceleration for the wall at that location.

Although a representative illustration of the methodology is given various modifications can be made without departing from the scope of the invention.

What is claimed is:

1. A method to collect and present cardiac medical information to a physician comprising:
    applying a set of surface patch electrodes to said patient;
    positioning an intracavitary electrode on a catheter placed in a heart of said patient;
    injecting current between pairs of said set of surface patch electrodes, defining driven electrode axes;
    measuring the voltage present on the intracavitary electrode due to the applied currents;
    resolving the location of the intracavitary electrode along each of the axes based upon the measured voltage on the intracavitary electrode;
    collecting multiple intracavitary electrode locations;
    selecting the exterior most locations and creating a shell based upon the exterior most locations generating a surface geometry; and
    presenting the surface geometry as an image to the physician.

2. The method of claim 1 further comprising the steps of:
    measuring voltage on the intracavitary electrode generated by the heart creating EP data;
    projecting the EP data on the surface geometry; and
    displaying the location of said intra-cardiac electrode on said image.

3. The method of claim 2 wherein:
    said EP data includes the peak to peak value of the voltage measurement.

4. The method of claim 3 wherein:
    said EP data includes a time value related to relative timing of the voltage measurement and a pre-selected fiducial time.

* * * * *